United States Patent [19]

Costerton et al.

[11] Patent Number: 4,800,959
[45] Date of Patent: Jan. 31, 1989

[54] MICROBIAL PROCESS FOR SELECTIVELY PLUGGING A SUBTERRANEAN FORMATION

[75] Inventors: J. William F. Costerton; Francene Cusack; Fraser A. MacLeod, all of Calgary, Canada

[73] Assignee: Alberta Oil Sands Technology and Research Authority, Edmonton, Calif.

[21] Appl. No.: 122,814

[22] Filed: Nov. 19, 1987

[51] Int. Cl.$^4$ ............... E21B 43/22; E21B 33/138
[52] U.S. Cl. .................... 166/246; 166/294; 435/852; 435/877
[58] Field of Search .............. 166/246, 294, 292; 405/263, 264; 435/260, 801, 852, 877

[56] References Cited

U.S. PATENT DOCUMENTS

| | | | |
|---|---|---|---|
| 4,250,264 | 2/1981 | Nelson et al. | 435/260 X |
| 4,350,769 | 9/1982 | Kang et al. | 435/852 X |
| 4,460,043 | 7/1984 | Thompson et al. | 166/246 |
| 4,558,739 | 12/1985 | McInerney et al. | 166/246 |

Primary Examiner—George A. Suchfield
Attorney, Agent, or Firm—Millen & White

[57] ABSTRACT

A microbial process is provided for selectively plugging a high permeability stratum or zone in a subterranean reservoir. Starved bacteria of reduced size are injected into the zone. A poor-nutrient media is either simultaneously or subsequently thereafter injected into the zone to substantially uniformly resuscitate the starved bacteria. Thereupon, the bacteria regain full cell size, proliferate, and commence production of biofilm-forming exocellular polysaccharides. The biofilm is functional to selectively seal off the high permeability zone of the formation and reduce aqueous flow through the zone.

4 Claims, 1 Drawing Sheet

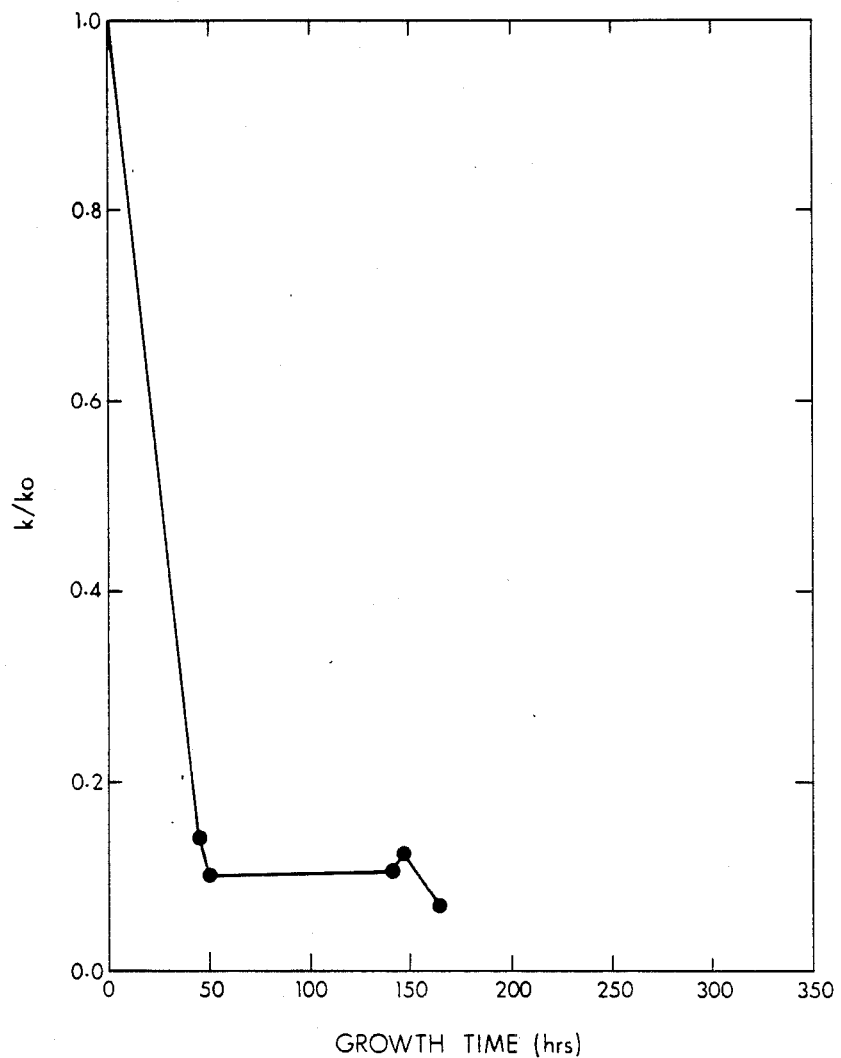
Fig.

MICROBIAL PROCESS FOR SELECTIVELY PLUGGING A SUBTERRANEAN FORMATION

FIELD OF THE INVENTION

The present invention relates to a microbial process for selectively plugging a permeable subterranean zone or stratum which is associated with an oil-bearing formation.

BACKGROUND OF THE INVENTION

In the course of some secondary oil recovery operations, water is injected through an injection well to sweep or drive oil toward an adjacent production well. A serious problem that can arise in such an operation is that the water preferentially moves through permeable strata in the formation and bypasses oil contained in less permeable strata. This narrowly focussed water movement is commonly referred to as "fingering". As a result of fingering, the "sweep efficiency" of many water-swept operations fall far short of what is sought.

Another water movement problem associated with oil recovery operations is referred to as "coning". When an oil well is being produced, water present in a stratum underlying the oil zone can "cone" upwardly and enter the well bore. As the difference in viscosity between the oil and water is usually significant, the water tends to move more easily through the rock or sand matrix adjacent the well bore. As a result, this flow of water excludes the oil from the well bore, which is undesirable.

Because of these problems, there is an ongoing search for an effective means for preventing the movement of water through certain zones or strata associated with an oil reservoir.

Various techniques have been applied in the past for this purpose. In general, the techniques involve plugging the high permeability strata with some fluidic material that remains in place and diverts water movement to the less permeable zones.

In connection with this approach, it is desirable:
that the plugging agent be 'selective', in the sense of concentrating in the high permeability strata;
and that it be adapted to create an effective plug that extends deeply enough along the longitudinal extent of the high permeability zone so that the water flow cannot quickly bypass it and re-enter the zone.

One of the methods which has been explored for the purpose of plugging a subterranean permeable zone involves the use of bacteria. Live bacteria in the vegetative state, when injected into a formation, can form adherent microcolonies on the surfaces of the pores and channels in the rock or sand matrix. These colonies produce exopolysaccharides that coalesce to form a confluent biofilm. This biofilm functions to impede aqueous flow through said pores and channels.

Laboratory studies have shown that bacteria biofilm can be effective to effectively seal a simulated reservoir matrix or core formed of fused glass beads. This is disclosed in a paper entitled 'Bacterial Fouling in a Model Core System' by J. C. Shaw et al in Applied and Environmental Microbiology, March, 1985, pages 693-701.

This paper further disclosed that when bacterial cultures were passed through a cylindrical fused-glass-bead core, the build-up of a thick biofilm took place at the inlet end of the core, whereas bacterial colonization of surfaces was very sparse in the lower areas of the core. Stated otherwise, the bacteria tended to quickly seal the inlet end of the core. This has been referred to as "skin plugging" and this result is referred to again below.

Additionally, it has been shown that when parallel reservoir cores of differing permeability were simultaneously subjected to the injection with a bacterial plugging agent, the more permeable pathway was first plugged. Stated otherwise, plugging with bacteria is selective of the permeable zone. This was disclosed in U.S. Pat. No. 4,558,739 issued to McInerney et al.

The McInerney patent went on to teach a process embodiment which is of particular interest with respect to the present invention. More particularly, the patent disclosed:
injecting bacterial spores into a permeable stratum to be plugged;
then injecting a solution (brine) which is capable of substaining spore viability while being inadequate to induce spore germination;
and then injecting nutrient solution to induce spore germination and bacterial proliferation.

The McInerney process was designed to emplace the spores deeply into the formation. Spores were used because they are small and non-adhesive in nature. The brine was used to displace them deeply into the rock or sand matrix. And the nutrient was used to resuscitate the emplaced spores and induce them to produce biofilm to plug the formation channels.

However, the McInerney process was subject to certain disadvantages.

As bacterial spores, which are metabolically inert spherical cells, are of 1 $\mu$m diameter, size constraints restrict the penetration thereof to rocks having a permeability of greater than 1 darcy. In a typical reservoir, there usually exist "fingering" zones, having a permeability less than 1 darcy, which require sealing off.

Further, in order to be successfully returned to the vegatative state, a species-specific nutrient is required or must be developed for each type of spore. Additionally, only a relatively small number of classes of Gram-positive bacteria exhibit spore-forming capability.

These factors limit the use of spores for plugging purposes.

Digressing somewhat, by way of background, to the field of marine microbiology, it has been known that, in a low nutrient environment, the cells of certain bacterial strains undergo significant reductions in cell size and morphological transformations during progressive cell divisions. These reduced-sized cells formed under a starvation regime are defined as 'ultramicrobacteria' (umb) or 'ultramicrocells'. The diameters of ultramicrobacteria range from about 0.2 $\mu$m to about 0.4 $\mu$m.

The isolation of ultramicrobacteria from deep ocean water was first discolsed by J. A. Novitsky and R. Y. Morita in 1977 in an article entitled 'Survival of a Psychrophilic Marine Vibrio under Long-Term Nutrient Starvation' in Applied Environmental Microbiology 33:635-641.

Subsequent experimental work has demonstrated that ultramicrobacteria can be prepared in the laboratory by simulating the starvation conditions found in low nutrient environments. It has further been observed that the ultramicrobacteria, although in a dormant condition, remain viable during starvation. Further, the dormant condition of some starved microorganisms has been demonstrated to be reversible. The supply of nutrient to the starved cells rapidly produces an increase in cell size, growth, cell division and a return to the original cell configuration. Stated otherwise, once fed, the starved cells may return to the vegetative adherent biofilm-forming state.

Applicants postulated that ultramicrobacteria had a better potential, because of their small size and lack of glycocalyx coating, for penetrating deeply into a relatively "tight" formation to effect plugging thereof, than had bacterial spores or live vegetative bacteria.

However, it will be readily appreciated that at this stage, although the response of marine and soil organisms to starvation and resuscitation had been explored, the responses of microorganisms from other environments were not understood.

It was not predictable:
that umb could be produced from naturally-occurring species of deep groundwater bacteria; or
that umb were sufficiently non-adhesive to penetrate the formation and be evenly distributed therethrough; or
that the umb could be effectively resuscitated in situ without "skin plugging"; or
that the produced biofilm would be effective to plug the stratum.

SUMMARY OF THE INVENTION

In accordance with the present invention, a microbial process is provided for selectively plugging a subterranean permeable stratum which is usually associated with an oil-bearing formation. The process comprises:
injecting into the stratum ultramicrobacteria having a diameter in the range of about 0.2 to about 0.4 $\mu$m; and
injecting a specific nutrient controlled solution into the stratum to substantially uniformly resuscitate said ultramicrobacteria to the vegetative state and cause them to produce biofilm functional to effect plugging of said stratum.

Preferably such ultramicrobacteria are formed by isolating a bacterial class indigenous to oil reservoir waters and subjecting said isolates to a starvation regime. Most preferably, the ultramicrobacteria are selected from the group consisting of the species *Pseudomonas putida* and *Klebsiella pneumoniae*.

In applications in which a rapid but shallow biofilm plug is required, we use a rich complex bacteriological medium designated ½ strength brain heart infusion. Where deeper and more even plugging is required, we use a chemically defined salt medium containing various amounts of trisodium citrate as a slowly-utilizable carbon source. In this way the extent of the plugged zone can be manipulated.

The invention is characterized by the following advantages:
the ultramicrobacteria penetrate deeply and are distributed generally uniformly in the reservoir matrix-the difficulty with "skin plugging" is resolved;
the ultramicrobacteria return to the vegetative state with injection of a relatively non-specific nutrient; and
saline-resistant bacteria which are indigenous to the subterranean reservoir can be isolated, starved, injected, and evenly resuscitated in situ to provide effective plugging.

DESCRIPTION OF THE DRAWINGS

The FIGURE is a plot of the permeability reduction (k/ko) for *Pseudomonas putida* versus growth time, through a sand pack core.

DESCRIPTION OF THE PREFERRED EMBODIMENT

Microorganisms which may be utilized in the practice of the invention include those classes of bacteria functional to adopt a reduction in cell size under starvation conditions (i.e. to produce ultramicrobacteria of diameter about 0.2 $\mu$m to about 0.4 $\mu$m) and, upon resuscitation to the vegetative state, to secrete biolfilm-producing exocellular polysaccharides. Bacterial isolates from oil reservoir waters are particularly suitable for the generation of suitable ultramicrobacteria. In particular, the species *Pseudomonas putida* and *Klebsiella pneumoniae* successfully produce the desired sealing biofilm.

The bacterial isolates are first grown to the stationary phase and harvested. The harvested isolates are then subjected to a starvation regime, until ultramicrobacteria having a diameter of about 0.2-0.4 $\mu$m are detected. Typically, the time required for starvation is about two to four weeks. The starvation media in which the vegetative bacteria are suspended comprises a carbon-poor medium. One suitable medium is an aqueous solution containing phosphate buffer salts (PBS), which contain (gl$^{-1}$ distilled water) NaCl, 8.5; KH$_2$PO$_4$, 0.61; K$_2$HPO$_4$, 0.96; pH, 7.0.

In carrying out the invention, the ultramicrobacteria are injected into the formation through a well in accordance with conventional practice.

Again, using conventional methods, a nutrient slug is injected into the formation to resuscitate the ultramicrobacteria emplaced therein. The nutrient media is usually a nutritionally 'poor' medium functional to resuscitate the ultramicrobacteria substantially uniformly throughout the formation, to thereby ensure growth of a deep bacterial plug. A suitable nutrient comprises, for example, sodium citrate solution containing (gl$^{-1}$ glass distilled water) Na$_3$C$_6$H$_5$O$_7$.2H$_2$O, 7.36; (NH$_4$)$_2$SO$_4$, 3.30; KH$_2$PO$_4$, 7.30; K$_2$HPO$_4$, 9.22; MgSO$_4$, 0.12; FeCl$_3$, 0.0041; pH 7.0.

Experimental

The invention is further disclosed by the following examples which are provided to demonstrate and support the operability of the present process.

Ultramicrobacterial Preparation

*Klebsiella pneumoniae* and *Pseudomonas putida* were isolated from produced reservoir water and identified by standard microbiological methods. The bacteria were grown, in 40 liters of solution, to the stationary phase (i.e. a growth of $1 \times 10^9$ cells/mL) in trisodium citrate medium (SCM) by the method as disclosed by Shaw et al. 'Bacterial Fouling in a Model Core System', Applied Environmental Microbiology, 50:693-701. The organisms were harvested by centrifugation (10,000$\times$g, 15 min., 4° C.) and washed in sterile phosphate buffer salts (PBS) twice to eliminate any transfer of nutrients into the starvation media. The PBS contained (gL$^{-1}$ distilled water), NaCl, 8.5; KH$_2$PO$_4$, 0.61, K$_2$HPO$_4$, 0.96; pH, 7. The cells were re-suspended in a sterile PBS starvation media. The starved cell suspension was stirred at 22 C at 200 rev. min$^{-1}$ for 2-4 weeks, until the cell sizes had reached a diameter of about 0.2-0.4 μm as determined by direct light and electron microscopy.

After 24 days of starvation cell sizes were determined by transmission electron microscopy (TEM). Confirmation of the viability of ultramicrobacteria was made by resuscitating the starved cells by inoculation (2% v/v) into both SCM and half strength Brain Heart Infusion medium (½ BHI) and the now-ascertainable cell sizes were monitored thereafter. The ultramicrobacteria solutions tested contained about ±1.0×10⁸ cells/ml and dilutions of this stable umb suspension can be made readily.

Example I

Glass bead (6-7 darcy) and sandstone (200 and 400 md) cores were used to determine plugging properties of a vegetative culture of Pseudomonas putida, isolated from a produced water source. The sintered glass bead cores were prepared as described by Shaw et al in Applied and Environmental Microbiology, March, 1985, pages 693-701, and the rock cores as described by Cusack et al. in the Journal of Petroleum Science and Engineering, volume 1, 1987, pages 39-50. Effluent volumes and flow rates were measured during vegetative culture injections to determine percent plugging by dividing the initial flow rate ($k_i$) by the final flow rates (K). Experiments were performed under a constant nitrogen pressure of 3.5 psi (24 KPA). The cultures were grown to stationary phase as described by Shaw et al in 6 l batch cultures of trisodium citrate medium prior to injection.

To examine biofilm development at the different core depths, the cores were fractured at various lengths and prepared for scanning electron microscopy, viable cell concentrations and carbohydrate analysis, as described by Shaw et al, supra.

The results of three experimental core runs using the Pseudomonas species are summarized in Table I. Core 1 was a 6-7 darcy glass bead core, Core 2 was a 200 md sandstone core, and core 3 was a 400 md sandstone core. All three cores were 5 cm in length. The sandstone cores were 1.5 cm in diameter and the glass bead core was 1.0 cm in diameter.

Initial concentrations of bacterial cultures were: core 1—1.0×10⁸ cells/ml; core 2—4.4×10⁸ cells/ml; and core 3—4.4×10⁸ cells/ml.

With respect to all three cores, it was evident that the greatest concentration of cells and carbohydrate production occurred at the top end of each core. The cell population and slime production rapidly decreased about 1.0 cm from the inlet surface. Visual observation of the scanning electron micrographs indicated a mass of bacteria encased in slime on the top section and scant throughout the length.

It was confirmed that injection of vegetative cells resulted in a skin plug at the inlet faces of the cores.

TABLE I
SUMMARY OF VIABLE CELL COUNTS AND CARBOHYDRATE PRODUCTION OF *PSEUDOMONAS PUTIDA*

|  |  | Viable Cells cell-ml | Carbohydrate μg/piece** |
|---|---|---|---|
| Core 1* | top | 72.7 × 10⁷ | 3469 |
|  | 1 cm | 72.7 × 10⁷ | 2542 |
|  | 2 cm | 3.4 × 10⁶ | 1410 |
|  | 3 cm | 1.1 × 10⁶ | 1530 |
|  | 4 cm | 1.8 × 10⁶ | 1650 |
| Core 2 | top | >3.0 × 10⁸ | 14000 |
|  | 1 cm | 1.04 × 10⁷ | 8640 |
|  | 2 cm | 1.04 × 10⁷ | 8640 |
|  | 3 cm | 9.7 × 10⁶ | 7920 |
|  | 4 cm | 1.08 × 10⁷ | 8320 |
| Core 3 | top | 73.0 × 10⁸ | 15520 |
|  | 1 cm | 1.24 × 10⁷ | 10320 |
|  | 2 cm | 1.04 × 10⁷ | 8320 |
|  | 3 cm | 1.14 × 10⁷ | 8200 |
|  | 4 cm | 1.22 × 10⁷ | 8320 |

*Core 1, 6-7 D glass bead core
Core 2 - 200 md sandstone core
Core 3 - 400 md sandstone core
**Core 1 piece = .39 cm³, Cores 1 & 2 piece = 2.01 cm³

Example II

This example is provided to illustrate the penetration profiles of the ultramicrobacteria into cores and to show the effects of nutrient resuscitation thereof in situ.

Each core was prepared by packing a stainless steel cell (10 cm in length by 1.27 cm in diameter) with −200 mesh Ottawa sand. The sand pack was purged with $CO_2$ gas and then saturated with deionized water. The permeability of the sand pack was 3.3 darcys.

Ultramicrobacteria of the *Pseudomonas putida* species were starved for 40 days in the manner described above.

10 pore volumes of the ultramicrobacteria were injected into the sand pack at a rate of 2 ml min. for approximately twenty-five minutes to ensure saturation of the core therewith.

Following umb injection 2-3 pore volumes of trisodium citrate nutrient solution, as previously described, was injected and locked in.

Changes in core permeabilities were determined by changes in pressure across the core during nutrient injection (10 minutes) at a constant flow rate of 2 ml/min. An increase in pressure indicated a decrease in permeability.

The experimental results of permeability reduction during resuscitation under nutrient stimulation are given in Table II herebelow and are illustrated in the figure appended hereto.

TABLE II

| | Growth Time (hr) | Pressure Drop (psi) | (kPa) | Permeability (ko) | k/ko |
|---|---|---|---|---|---|
| 1 | 0.00 | 1.0 | 6.894760 | 3.30 | 1.000000 |
| 2 | 45.00 | 6.9 | 47.573844 | 0.47 | 0.142424 |
| 3 | 50.25 | 9.7 | 66.879172 | 0.34 | 0.103030 |
| 4 | 141.50 | 9.1 | 62.742316 | 0.36 | 0.109091 |
| 5 | 147.00 | 7.7 | 53.089652 | 0.42 | 0.127273 |
| 6 | 164.50 | 13.7 | 94.458212 | 0.24 | 0.072727 |

Species—*Pseudomonas putida*—starved for 40 days—start culture had a concentration of 2.7×10⁷ cells/ml.

During the experimental run, effluent samples were analyzed for viable cells passing through the core.

The following data were obtained:

Viable Cell Counts

During bacteria injection: Day 1
 10 minutes: 3.8×10⁶ cells/ml
 20 minutes: 51.×10⁶ cells/ml
During nutrient injection: Day 2

5 minutes: $2.5 \times 10^6$ cells/ml

Samples Taken During Plugging Phase

|   | Date         |       | Cell Counts                   |
|---|--------------|-------|-------------------------------|
| A | June 25 a.m. | Day 2 | $3.4 \times 10^6$ cells/ml    |
| B | June 25 p.m. | Day 2 | $2.21 \times 10^8$ cells/ml   |
| C | June 26 a.m. | Day 3 | $4.14 \times 10^8$ cells/ml   |
| D | June 26 p.m. | Day 3 | $1.14 \times 10^8$ cells/ml   |
| E | June 30 a.m. | Day 7 | $6.7 \times 10^7$ cells/ml    |
| F | June 30 p.m. | Day 7 | $9.7 \times 10^7$ cells/ml    |
| G | July 1 a.m.  | Day 8 | $3.2 \times 10^7$ cells/ml    |

When the run was completed (permeability reduction had reached 93%), the core was cut into 11 sections. Each such section was sub-divided in 3 sub-sections. The 3 subsections were separately used for one of viable cell count carbohydrate analysis and scanning electron microscopy, to determine cell penetration through the length of the core, the stimulation of cell and polymer production in the core and the relative distribution of cells. The results are recorded as per gram of sand in Table III.

TABLE III

| Core Sections | | |
|---|---|---|
| Section | Viable Cells | Carbohydrate |
| 1. | $2.30 \times 10^8$ cells/gram | 1789.47 mg/g (glucose*) |
| 2. | $5.00 \times 10^8$ cells/gram | 4166.67 mg/g |
| 3. | $3.24 \times 10^8$ cells/gram | 3200.00 mg/g |
| 4. | $8.18 \times 10^8$ cells/gram | 1176.47 mg/g |
| 5. | $7.27 \times 10^8$ cells/gram | 1488.37 mg/g |
| 6. | $3.75 \times 10^8$ cells/gram | 1304.35 mg/g |
| 7. | $3.75 \times 10^8$ cells/gram | 1478.26 mg/g |
| 8. | $3.53 \times 10^8$ cells/gram | 1090.91 mg/g |
| 9. | $2.46 \times 10^8$ cells/gram | 1463.41 mg/g |
| 10. | $1.32 \times 10^8$ cells/gram | 447.76 mg/g |
| 11. | $1.60 \times 10^8$ cells/gram | 536.01 mg/g |

*Carbohydrate assay: numbers expressed as (mg/g) of glucose.

The results indicate:
(1) that the starved cells penetrated the full length of the core;
(2) that the nutrient stimulated the growth and polymer production of the starved cells;
(3) that substantially even growth and concomitant plugging occurred through the entire length of the core; and
(4) that each of the viable cell and carbohydrate counts were very high, indicating that most of the available pore space was occupied by biofilm material.

It follows that injection of metabolically-inert, substantially spherical, generally non-adhesive ultramicrobacteria will penetrate reservoir sand relatively deeply and with substantially even distribution, when compared to the results obtained when vegetative bacteria are injected. Also, it has been demonstrated that the ultramicrobacteria can be returned to the vegetative state in situ with nutrient and then function to effectively plug the sand matrix.

Example III

This example is given to provide a comparison of the effects of utilizing a 'poor' nutrient solution and a 'rich' nutrient solution, to resuscitate in situ ultramicrobacteria.

Ten cylindrical sandstone cores (5.0 cm in length and 1.0 cm in diameter) of known permeability (200–400 mD) were prepared. Each core was gas sterilized for 4 to 5 h with ethylene oxide and soaked in filtered PBS in a vacuum chamber for 40 mins. The cores were than wrapped in Teflon tape, covered in silicon grease and inserted into rubber core holders.

Ultramicrobacteria prepared as described hereinabove were injected through the cores under nitrogen pressure of 25 kiloPascals (kPa) using the apparatus described by Shaw et al. supra.

The cores were subjected to separate treatments as summarized in Table IV given herebelow.

TABLE IV

| | | A Summary of Core Treatments | | | | | |
|---|---|---|---|---|---|---|---|
| Core Number | Initial Permeability (md) | Treatment | Initial Viable Cell Count (ml$^{-1}$) | Pore Volumes (PV) | Reduction in Permeability (%) | Nutrient Treatment | Permeability Reduction After Nutrient Treatment (%) |
| 1 | 400 | Starved Cells | $1.1 \times 10^6$ | 630 | 4 | — | — |
| 2 | 400 | Starved Cells | $8.4 \times 10^4$ | 286 | 18 | 364 PV SCM continuous | 0.1 |
| 3 | 400 | Starved Cells | $3.7 \times 10^5$ | 455 | 13 | 47 PV SCM locked-in | 3.9 |
| 4 | 400 | Starved Cells | $7.1 \times 10^5$ | 318 | 15 | 95 PV SCM continuous | 0.5 |
| 5 | 400 | Starved Cells | $3.7 \times 10^5$ | 380 | 16 | 4 PV ½BHI locked-in | 2.2 |
| 6 | 200 | Starved Cells | $1.0 \times 10^5$ | 1800 | 16 | — | — |
| 7 | 200 | Starved Cells | $1.0 \times 10^5$ | 640 | 24 | 170 PV SCM continuous | 4.0 |
| 8 | 400 | Starved Cells | $2.0 \times 10^6$ | 340 | 40 | 415 PV SCM continuous | 0.2 |
| 9 | 400 | Starved Cells | $1.2 \times 10^6$ | 930 | 60 | 1260 PV SCM continuous | 0.2 |
| 10 | 400 | Starved Cells | $2.4 \times 10^6$ | 150 | 81 | 1160 PV SCM continuous | 1.0 |

Cores 1 to 10 were injected with starved *K. pneumoniae*. Numbers 1 to 6 were control experiments and were treated with starved cells only until the maximum reductions in core permeability were achieved. Cores 2 to 5 and 17 were plugged with starved cells until the permeability was approximately 20%. Each core was then injected with either SCM or half strength Brain Heart Infusion medium (½ BHI). The nutrients were injected either as a continuous flow until the cores were plugged or as a single injected amount and then locked into the core.

The permeabilities of cores 8, 9 and 10 were reduced to approximately 40%, 60% and 80% respectively with starved cells. Each core was then injected with a continuous flow of SCM until the final core permeability was less than 2%.

After each core treatment was completed the cores were removed from the holders and cut along the length by shallow scoring with a diamond blade saw followed by a razor blade. Each section was further divided into subsections. Core pieces were prepared for scanning electron microscopy (SEM) by critical point drying and gold-palladium coating as is known in the art. Viable cell counts of core pieces of known weight were undertaken by sonicating the crushed core pieces in 5.0 ml PBS for 3×30 seconds bursts then spread plating the solution onto ½ BHI agar. The plates were incubated before the colony forming units counted.

The results are given in Table V herebelow.

TABLE V

Viable Counts of *K. pneumoniae* at Various Core Depths

| Core Depth (cm) | Viable Cell Counts × $10^8$ ml[1]* | | | | |
|---|---|---|---|---|---|
| | Core 5 | Core 7 | Core 8 | Core 9 | Core 10 |
| 1.0 | 8.4 | 15.3 | 22.7 | 28.6 | 42.7 |
| 2.0 | 2.1 | 8.9 | 22.0 | 23.8 | 23.1 |
| 3.0 | $7.6 \times 10^6$ | 7.4 | 21.7 | 24.7 | 21.7 |
| 4.0 | $3.1 \times 10^6$ | 4.0 | 21.6 | 27.5 | 17.9 |
| 5.0 | $3.6 \times 10^5$ | 6.0 | 16.4 | 22.4 | 19.4 |

*1.0 g of sandstone core pieces were crushed and sonicated in 5.0 ml PBS.

The viable count data (Table V) clearly show that flooding of the core with umb and subsequent nutrient stimulation with a rich complex medium (core 5) plugs the core to 2% permeability but produces a thin plug—$8.4\times10^8$ cells/ml at the inlet and $3.6\times10^5$ cell/ml at 5 cm depth. In contrast, flooding of the cores with umb, to varying levels of permeability reduction (24–81% of original), and subsequent nutrient stimulation using a less rich trisodium citrate "package", produced a very effective plugging that extended through the 5 cm length of the core (cores 7–10).

These data illustrate that poor nutrients provide deep plugging in this bacterial modification of stratum permeability.

The embodiments of the invention in which an exclusive property or privilige is claimed are defined as follows:

1. A process for plugging a permeable subterranean stratum which comprises:

injecting ultramicrobacteria into the stratum, said ultramicrobacteria having a diameter in the range of about 0.2 μm to about 0.4 μm; and injecting a nutrient-containing solution into the stratum, said solution being adapted to substantially uniformly resuscitate the ultramicrobacteria to the vegetative state and cause them to produce sufficient biofilm to effectively plug said stratum.

2. A process for plugging a permeable subterranean stratum which comprises:

isolating from oil reservoir waters a class of bacteria indigenous thereto;

starving the bacteria until the cells have reached a diameter less than about 0.4 μm;

injecting the produced ultramicrobacteria into the stratum; and injecting a nutrient-containing solution into the stratum, said solution being adapted to substantially uniformly resuscitate the ultramicrobacteria to the vegetative state and cause them to produce sufficient biofilm to effectively plug said stratum.

3. The process as set forth in claim 1 wherein:

the bacteria are selected from the group consisting of *Pseudomonas putida* and *Klebsiella pneumoniae;* and trisodium citrate is the nutrient.

4. The process as set forth in claim 2 wherein:

the bacteria are selected from the group consisting of *Pseudomonas putida* and *Klebsiella pneumoniae;* and trisodium citrate is the nutrient.

* * * * *

UNITED STATES PATENT AND TRADEMARK OFFICE
CERTIFICATE OF CORRECTION

PATENT NO. : 4,800,959
DATED : January 31, 1989
INVENTOR(S) : Costerton et al

It is certified that error appears in the above-identified patent and that said Letters Patent is hereby corrected as shown below:

Title Page, Inventors:

Reads:   "J. William F. Costerton; Francene Cusack; Fraser A. MacLeod, all of Calgary, Canada"

should Read:   --J. William F. Costerton; Francene Cusack; Fraser A. MacLeod, all of Calgary; Theodore J. Cyr, Edmonton, Canada--

Signed and Sealed this

Eighteenth Day of July, 1989

Attest:

DONALD J. QUIGG

*Attesting Officer*      *Commissioner of Patents and Trademarks*